United States Patent [19]

Somberg

[11] Patent Number: 6,103,757
[45] Date of Patent: Aug. 15, 2000

[54] METHODS FOR TREATING ARRHYTHMIA USING ACETATE BUFFER SOLUTIONS OF AMIODARONE

[75] Inventor: John C. Somberg, Lake Forest, Ill.

[73] Assignee: Academic Pharmaceuticals, LP, Lake Bluff, Ill.

[21] Appl. No.: 09/390,295

[22] Filed: Sep. 3, 1999

Related U.S. Application Data

[63] Continuation of application No. 08/884,354, Jun. 27, 1997, abandoned.

[51] Int. Cl.$^7$ .................................................. A61K 31/34
[52] U.S. Cl. ......................... 514/469; 514/337; 514/422; 514/232.5
[58] Field of Search .................................. 514/469, 337, 514/422, 232.5

[56] References Cited

U.S. PATENT DOCUMENTS

| | | |
|---|---|---|
| 3,248,401 | 4/1966 | Tondeur et al. . |
| 4,791,137 | 12/1988 | Descamps et al. . |
| 5,234,949 | 8/1993 | Ehrenpreis et al. . |

FOREIGN PATENT DOCUMENTS

| | | |
|---|---|---|
| 133176 | 2/1985 | European Pat. Off. . |
| 338746 | 10/1989 | European Pat. Off. . |
| 2280 | 1/1964 | France . |
| WO 90/09171 | 8/1990 | WIPO . |
| WO 93/19753 | 10/1993 | WIPO . |

OTHER PUBLICATIONS

Anderson, "Current understanding of lidocaine as an antiarrhythmic agent: A review," *Clin. Ther.* (1984) 6(2):125–41.

Bopp et al., "Acute hemodynamic effects of intravenous amiodarone in patients with coronary artery disease," *J. Cardiovasc. Pharmacol.,* (1985) 7(2):286–9.

Escoubet et al., "Suppression of arrhythmias within hours after a single oral dose of amiodarone and relation to plasma and myocardial concentrations," *Am. J. Cardiol.,* (1985) 55(6):696–702.

Gallik et al., "Hemodynamic and electrocardiographic effects of amio–aqueous, a new formulation of intravenous amiodarone," *PACE Pacing and Clinical Electrophysiology,* P1120 abs 283A (1997) 20(4)Part II.

Gallik et al., "Favorable hemodynamic effect of amio–aqueous, a new formulation of intravenous amiodarone," *Circulation,* (1997) 96(8)Suppl:1–383.

Gough et al., "Hypotensive action of commercial intravenous amiodarone and polysorbate 80 in dogs," *J. Cardiovasc. Pharmacol.,* (1982) 4(3);375–80.

Hardman et al., editors, Goodman & Gilman's *Pharmacological Basis of Therapeutics,* 9$^{th}$ Edition, McGraw–Hill, New York (1996) p. 866.

Hargarten, et al., "Prehospital prophylactic lidocaine does not favorably affect outcome in patients with chest pain," *Annals of Emergency Medicine,* (1990) 19(11):1274–9.

Kadish et al., "The use of intravenous amiodarone in the acute therapy of life–threatening tachyarrhythmias," *Prog. Cardiovasc. Dis.,* (1989) 31(4):281–94.

Kosinski et al., "Hemodynamic effects of intravenous amiodarone," *J. Am. Coll. Cardiol.,* (1984) 4(3):565–70.

Kowey et al., "Randomized, double–blind comparison of intravenous amiodarone and bretylium in the treatment of patients with recurrent, hemodynamically destabilizing ventricular tachycardia or fibrillation," *Circulation,* (1995) 92(11):3255–63.

Levine et al., "Intravenous amiodarone for recurrent sustained hypotensive ventricular tachyarrhythmias," *J. Am. Choll. Cardio.,* (1996) 27(1):67–75.

Morady et al., "Clinical characteristics and results of electrophysiologic testing in young adults with ventricular tachycardia or ventricular fibrillation," *Am. Heart J.,* (1983) 106(6):1306–14.

Mostow et al., "Rapid suppression of complex ventricular arrhythmias with high–dose oral amiodarone," *Circulation,* (1986) 73(6):1231–8.

*Physicians' Desk Reference,* (1992) p. 2446.

Ravin et al., "Micelle formation and its relationship to solubility behavior of 2–butyl–3–benzofuranyl–4–[2–(diethylamino)ethoxy]–3,5–diiodophenyl ketone hydrochloride," *J. Pharm. Sci.,* (1975) 64(11):1830–3.

*Remington's Pharmaceutical Sciences,* 17$^{th}$ Edition, (1985) pp. 1521–1523.

Remme et al., "Hemodynamic effects of tolerability of intravenous amiodarone in patients with impaired left ventricular function," *Am. Heart J.,* (1992) 122:96–103.

Scheinman et al., "Dose–ranging study of intravenous amiodarone in patients with life–threatening ventricular tachyarrhythmias," *Circulation,* (1995) 92(11):3264–72.

Somberg, "Intravenous amiodarone," *Clinical Progress in Electrophysiology and Pacing,* (1986) 4(5):430–5.

Somberg et al., "A new aqueous preparation of amiodarone", *Circulation,* (1995) 92(8)Suppl:I–195.

Somberg et al., "A new aqueous preparation of amiodarone," *J. of Inv. Med.* (1995) 43(3)Suppl:A–430.

Torres–Arrault et al., "Electrophysiological effects of tween 80 in the myocardium and specialized conduction system of canine heart," *J. Electrocardiology,* (1984) 17(2):145–152.

*Primary Examiner*—James H. Reamer
*Attorney, Agent, or Firm*—McDonnell Boehnen Hulbert & Berghoff

[57] ABSTRACT

Disclosed herein are methods for treating human patients suffering from arrhythmia comprising administration to the human a solutions containing a 3-diethylaminoethoxybenzoyl-benzofuran in acetate buffer.

8 Claims, No Drawings

METHODS FOR TREATING ARRHYTHMIA USING ACETATE BUFFER SOLUTIONS OF AMIODARONE

REFERENCE TO RELATED APPLICATIONS

This application is a continuation of application Ser. No. 08/884,354, filed Jun. 27, 1997 now abandoned.

BACKGROUND OF THE INVENTION

1. Field of the Invention

The present invention relates to the use of parenteral solutions containing 3-diethylaminoethoxybenzoylbenzofurans in the treatment of arrhythmia. More specifically, the present invention relates to the use of a parenteral solution of 2-n-butyl-3-(3, 5-diiodo-4-(P-N-diethylaminoethoxy)benzoyl)benzofuran in the treatment of arrhythmia.

2. Description of the Related Art 2-n-butyl-3-(3,5-diiodo-4-(β-N-diethylaminoethoxy) benzoyl) benzofuran [4-(2-(diethyl-amino)ethoxy)-3,5-diiodophenyl 2-butylbenzo[b]furan-3-yl ketone] (hereinafter amiodarone) has been approved in an oral tablet form (CORDARONE®) for the treatment of life-threatening ventricular tachyarrhythmias in the United States since 1985. This drug is useful not only in treating these arrhythmias but also in treating less severe ventricular arrhythmias and many supraventricular arrhythmias including atrial fibrillation and reentrant tachyarrhythmias involving accessory pathways.

To treat arrhythmias, the compound may be administered in oral dosage forms such as in the form of a 200 mg tablet, or it may be administered in the form of an intravenous solution. See, for example, Escoubet, B. et al., "Suppression of Arrhythmias Within Hours After Single Oral Dose of Amiodarone and Relation to Plasma and Myocardial Concentrations", Am. J. Cardiol., (1985), 55:696–702, Mostow et al., "Rapid Suppression of Complex Ventricular Arrhythmias With High-Dose Oral Amiodarone", Circulation, (1986), 73:1231–8, Morady et al., "Intravenous Amiodarone in the Acute Treatment of Recurrent Symptomatic Ventricular Tachycardia", Am. J. Cardiol., (1983), 51:156–9 and Kadish et al. "The Use of Intravenous Amiodarone in the Acute Therapy of Life-Threatening Tachyarrhythmias". Progress in Cardiovascular Diseases, (1989), 31:4, 281–294.

Amiodarone is practically insoluble or slightly soluble in an aqueous solvent. Hence, it is difficult to formulate a dosage form suitable for intravenous administration. To aid the dissolution in water, for example, a surfactant has been suggested. Thus, the prior art intravenous dosage form for this compound, termed I.V. Cordarone, comprises amiodarone dissolved in a solvent comprising polysorbate 80 available under the tradename Tween-80, and benzyl alcohol. Prior art intravenous solutions of amiodarone will be designated IV Cordarone herein.

However, the use of this dosage form is highly undesirable because it exhibits deleterious cardiovascular effects attributable to the detergent. For example, Torres-Arrault et al. reported in Journal of Electrocardiology, 17 (2), 1984, pp 145–152 that Tween-80 is a potent cardiac depressant and causes hypotension in a dog. See also Gough et al., "Hypotensive Action of Commercial Intravenous Amiodarone and Polysorbate 80 in Dogs", Journal of Cardiovascular Pharmacology, (1982), 375–380. Further, Tween-80 is known to have anti-arrhythic action. See Torres-Arrault, J. Electrocardiology, 17 (2), 1984, pp. 145–152 and Yasaka, et al., Cardiovascular Research 1979; 13: pp. 717–722.

Kosinzki, et al., Am. J. Cardiol., (1984) 4: 565–70 report that intravenous amiodarone (IV Cordarone) can result in significant impairment of left ventricular performance in patients with pre-existing left ventricular dysfunction. After acute intravenous bolus administration, patients with a left ventricular ejection fraction greater than 0.35 experienced improved cardiac performance due to both acute and chronic peripheral vasodilation. However, patients with a lower ejection fraction developed a 20% decrease in cardiac index and clinically significant elevation of right heart pressures after acute bolus administration.

Remme et al., Am. Heart J., (1991) 122: 96–103 report that intravenous amiodarone caused a 15% reduction in blood pressure and an 18% increase in heart rate, and a progressive reduction in contractility (V sub max) with a rise in left ventricular and diastolic pressure.

Bopp et al., J. Cardio. Pharmacol., (1985) 7: 286–289 report that IV cordarone caused a decrease in the ejection fraction, an increase in pulmonary wedge pressure and a 15% decrease in dP/dt, and a 12% decrease in left ventricular work.

Each of the above three references discuss the effects of intravenous amiodarone (IV Cordarone), i.e., amiodarone solubilized for intravenous administration using polysorbate 80 and benzyl alcohol.

Both Tween 80 and benzyl alcohol have been required for dissolving amiodarone in prior art preparations. However, both Tween 80 and benzyl alcohol are known to cause hypotension, Munoz et al., European Heart Journal, (1988) 9: pp. 142–148; Varma, et al., Arzneim. Forsch (1985) 35(5), pp. 804–808. Also, the use of such prior art formulations in clinical studies has resulted in a clinically significant incidence of hypotension and resulting death. Scheinman, et al., Circulation (1995) 92: pp. 3264–3272; Levine et al. J. Am. Co. Cardiol. (1996) 27(1): 67–75; Mooss, et al., Am. J. Cardiol. (1990) 65: pp. 609–614; Kowey, et al., Circulation (1995) 92: pp. 3255–3263.

Further, Tween 80 is known to exert anti-arrhythmic action, as noted by Yasaka et. al., Cardiovascular Research (1979) 13: pp. 717–722.

U.S. Pat. No. 3,248,401, the disclosure of which is incorporated herein by reference in its entirety, issued Apr. 26, 1966 describes the preparation of 3-diethylaminoethoxybenzoyl benzofurans.

U.S. Pat. No. 5,234,949 discloses an amiodarone in acetate buffer formulation.

Physicians' Desk Reference, 1992, page 2446 under tradename Cordarone (r), provides the prescribing information relating to the oral form of this important product.

The Torres-Arrault, Taska and Gough articles described above set forth the hypotensive effects following intravenous administration of IV Cordarone (amiodarone in Tween-80).

The article "Intravenous Amiodarone", Clinical Progress in Electrophysiology and Pacing, (1986), 4:5, page 433 concludes that "Amiodarone, when administered intravenously, appears to have a rapid onset of action causing profound hemodynamic and electrophysiological effect.".

SUMMARY OF THE INVENTION

It has been unexpectedly discovered that intravenous administration of a parenteral solution of amiodarone in acetate buffer that is free of any Tween 80 exerts excellent anti-arrhythamic action without causing any concomitant hypotension in human patients. Thus, the present invention provides a method of treating a human suffering from arrhythmia employing a parenteral solution of amiodarone that is free of any Tween 80 which overcomes the disadvantages of prior art formulations of amiodarone.

In a first aspect, the invention provides methods for treating arrhythmias in humans comprising administering to the human an amount effective of a compound of the formula:

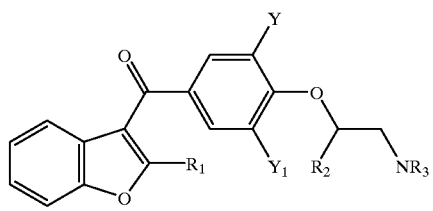

wherein
  $R_1$ represents alkyl of 1–6 carbon atoms;
  $R_2$ is hydrogen or methyl; and
  $R_3$ is dimethylamino, diethylamino, dipropylamino, piperidino, pyrrolidino or morpholino, and
  Y and $Y_1$ are hydrogen, iodo or bromo, the compound being dissolved in a buffer at a concentration of from about 10–50 mg/ml.

In another aspect of the invention, the patient is administered a parenteral solution suitable for intravenous administration containing as an active ingredient 2-n-butyl-3-(3, 5-diiodo-4-(β-N-diethylaminoethoxy)benzoyl) benzofuran (amiodarone) in a sterile solvent comprising an acetate buffer having a pH from about 3.5–4.0, i.e., an amiodarone-acetate buffer solution.

DETAILED DESCRIPTION OF THE INVENTION

According to the present invention, there is provided a method for the treatment of a patient, i.e., a human, suffering from arrhythmia comprising intravenously administering to the patient an effective antiarrhythmic quantity of a compound of the formula:

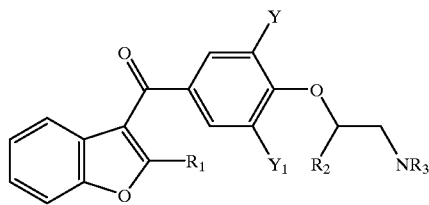

wherein
  $R_1$ is alkyl of 1–6 carbon atoms;
  $R_2$ is hydrogen or methyl; and
  $NR_3$ is dimethylamino, diethylamino, dipropylamino, piperidino, pyrrolidino or morpholino; and
  Y and $Y_1$ are hydrogen, iodo or bromo.

In preferred embodiments the compound is amiodarone, i.e., 2-n-butyl-3-(3,5-diiodo-4-(β-N-diethylaminoethoxy) benzoyl) benzofuran. In these preferred embodiments, the compound is dissolved in acetate buffer having a pH of from about 3.5 to 3.8 at a concentration of about 10 mg/ml to about 50 mg/ml. Typically, the compound is dissolved in about 0.05 to 0.1M acetate buffer. A more preferred method of the invention comprises intravenous administration of a solution comprising as an active ingredient about 15 to 50 mg/ml of amiodarone in about 0.05 to 0.1M acetate buffer solution having a pH of about 3.5 to 3.8. Another more preferred method of the invention comprises intravenous administration of a solution comprising as an active ingredient about 10–20 mg/ml of amiodarone in about 0.05 to 0.1M acetate buffer solution having a pH of about 3.5 to 3.8. A particularly preferred embodiment of the invention comprises intravenous administration of a solution comprising as an active ingredient about 10 to 20 mg/ml of amiodarone in about 0.05 to 0.1M acetate buffer solution having a pH of about 3.5 to 3.8. Especially preferred is a method comprising intravenous administration of a solution of about 15 mg/ml of amiodarone at the above pH and acetate concentrations.

In typical practice, an effective anti-arrhythmic amount of amiodarone in solution is administered intravenously to the patient. Effective amounts of the parenteral solution administered according to the invention do not cause hypotension in patients. See Table 1 below.

The preferred methods of the invention employ bolus intravenous administration of from about 150 to 300 mg of amiodarone dissolved in an acetate buffer solution having the concentrations of components and pH values as specified above.

In certain situations, the method will comprise intravenous administration of about 150 mg of amiodarone as a single bolus dosage. Alternatively, and somewhat more preferably, the inventive method employs intravenous administration of about 300 mg of amiodarone in two 150 mg bolus dosages.

The parenteral solution may be prepared as described in U.S. Pat. No. 5,234,949. As indicated in that patent, amiodarone HCl, which may be purified and crystalline, is dissolved in a buffer system comprising a weak acid and a salt of the weak acid, and more particularly a combination of acetic acid and sodium acetate having a pH below 4 and in particular at a range of about 3.5 to 3.8 and a molar concentration of about 0.05 to about 0.1M. An effective anti-arrhythmic amount of amiodarone, e.g., about 10–75 mg/ml, is mixed together with the buffer and heated to a temperature not to exceed about 75 degree(s) C., i.e., from about 60 degree(s) to 75 degree(s) C. and preferably from about 60 degree(s) to 65 degree(s) C. until solution is complete. This procedure is done under sterile conditions. Thereafter, the resulting solution is cooled to room temperature. Sterilization is maintained by ultrafiltration following sterile fill and packaged into ampules/vials suitable for dispensing as parenteral products. The resulting solution is stable when stored, for example, in ampules, at concentrations of from about 10 mg/ml to about 50 mg/ml over 24 months.

It is noted that solutions having amiodarone concentrations of between 1 and 5 mg/ml and above about 75 mg/ml are not stable; such solutions form a precipitate during accelerated stability tests after about 30 days.

The preparation thus obtained was found, quite surprisingly, to remain in solution, which of course is an important attribute for a product for intravenous administration. In fact, the product shows remarkable stability when stored at room temperature over a 4 month period without the formation of turbidity or precipitate.

The solution thus formulated is indicated for the treatment of humans suffering from life-threatening, sustained ventricular tachycardia or fibrillation without the fear of the undesirable side effects observed with the administration of a solution of amiodarone in Tween-80.

One skilled in the art will recognize that modifications may be made in the present invention without deviating from the spirit or scope of the invention. The invention is illustrated further by the following examples which are not to be construed as limiting the invention or scope of the specific procedures or compositions described herein.

EXAMPLE 1

Solubilization of Amiodarone in An Aqueous Solution

The vehicle for dissolving amiodarone consists of about 0.05 to 0.1 M acetate buffer with the pH in the range of about 3.5 to 3.8. As an example, to make a 50 mg/ml amiodarone solution, one ml of the buffer is added to 50 mg of the compound in a vial and the preparation is mixed using a mixer such as a Vortex mixer. Next the preparation is heated in a water bath such that the contents of the vial (buffer and amiodarone) does not exceed about 75 degree(s) C., i.e., from about 60 degree(s) to 75 degree(s) C. and preferably from about 60 degree(s) to 65 degree(s) C. The preparation is then cooled to room temperature. Amiodarone dissolved in the new vehicle remains in solution at room temperature in concentrations of about 25 to 50 mg/ml for an extended period of time.

EXAMPLE 2

Characteristics and Attributes of the Preparation of Example 1

The most important characteristic of the amiodarone-acetate buffer preparation is that amiodarone remains in solution. To analyze solution stability, solutions of about 15 to 75 mg/ml, preferably about 25 mg/ml, amiodarone were prepared as described in Example 1 and maintained at room temperature. The solutions were examined periodically over a period of four months following preparation; the solutions remained perfectly clear, i.e., no sign of turbidity or precipitate. However, at a pH above 4.0 a gel formed at room temperature.

Evaluation of the amiodarone-acetate buffer solution developed through this process demonstrates that the physical and chemical properties of amiodarone remain unchanged as determined by HPLC. As shown HPLC tracings, the peak of amiodarone dissolved in polysorbate 80 (Tween-80) is identical to the peak observed for the amiodarone HCl in the acetate buffer of the present invention. The tween-80 peak of the former preparation is clearly visible, this being the only difference between the two HPLC tracings.

EXAMPLE 3

Preparation of An Intravenous Dosage Form

A solution prepared according to Example 1 is sterilized, sealed using a sterile ultrafiltration membrane, and packaged into a sterile glass ampule and sealed under aseptic conditions giving a dosage form suitable for intravenous injection and containing about 25–50 mg/ml of amiodarone.

EXAMPLE 4

Intravenous Administration of Amiodarone to Humans

Amiodarone, 15 mg/ml in pH 3.5–3.8 acetate buffer, was administered intravenously (bolus) to patients suffering from ventricular tachycardia (VT) in either a single 150 mg bolus or two 150 mg bolus dosages (total dosage either 150 or 300 mg, respectively). Patients were monitored for hypotension and termination of VT.

As shown in Table 1 below, intravenous bolus administration of solutions containing about 15 mg/ml amiodarone in pH 3.5–3.8 acetate buffer do not cause hypotension in arrhythmic patients. The results of this study also demonstrate that bolus administration of the amiodarone solutions significantly terminates VT. See Table 2. In summary, efficacy of the first amiodarone bolus was about 35% and the efficacy of the second bolus was about 15%. Overall efficacy for the two bolus dosages is about 47%.

TABLE 1

The effect of 15 mg/ml amiodarone[1] on Mean Arterial Blood Pressure (BP)

| Patient No. | Baseline BP | BP Post 1st dose | BP Post 2nd dose | BP 30 min. after 1st dose |
|---|---|---|---|---|
| 1 | 72 | 82 | 73 | 91 |
| 2 | 85 | 91 | 84 | 98 |
| 3 | 82 | 91 | 98 | 88 |
| 4 | 96 | 107 | 113 | 125 |
| 5 | 76 | 78 | 93 | 78 |
| 6 | 104 | 119 | 118 | 122 |
| 7 | 105 | 107 | 102 | 116 |
| 8 | 80 | 59 | 89 | 96 |
| 9 | 89 | 115 | 103 | 99 |
| 10 | 92 | 96 | 95 | 109 |
| 11 | 72 | 71 | 74 | 82 |
| 12 | 119 | 117 | 120 | 125 |
| 13 | 95 | 105 | 108 | 104 |
| 14 | 94 | 97 | 97 | 105 |
| 15 | 75 | 86 | 86 | 85 |
| 16 | 80 | 90 | 93 | 89 |
| 17 | 86 | 84 | not available | 82 |
| 18 | 95 | 98 | 93 | 97 |
| 19 | 98 | 76 | 91 | 81 |
| 20 | 95 | 85 | 80 | 75 |
| 21 | 104 | 116 | 130 | 134 |
| 22 | 105 | 108 | 103 | 119 |
| 23 | 95 | 103 | 115 | 117 |
| Mean ± STD | 91 ± 12 | 94 ± 16 | 98 ± 15 | 100 ± 17 |

[1]Patients received a total dose of 300 mg amiodarone in 0.05M acetate buffer, pH 3.5–3.8. 1st dose: 150 mg amiodarone at 15 mg/ml; 2nd dose: 150 mg amiodarone at 15 mg/ml.

TABLE II

The Efficacy of Amiodarone in Man[2]

| Patient No. | 1st Bolus of 150 mg | 2nd Bolus of 150 mg |
|---|---|---|
| 1 | No | — |
| 2 | No | No |
| 3 | Yes | — |
| 4 | No | Yes |
| 5 | No | Yes |
| 6 | Yes | — |
| 7 | Yes | — |
| 8 | No | No |
| 9 | No | No |
| 10 | No | No |
| 11 | Yes | — |
| 12 | No | No |
| 13 | No | No |
| 14 | Yes | — |
| 15 | No | No |
| 16 | No | No |

TABLE II-continued

The Efficacy of Amiodarone in Man[2]

| Patient No. | 1st Bolus of 150 mg | 2nd Bolus of 150 mg |
|---|---|---|
| 17 | yes | — |
| 18 | Yes | — |
| 19 | No | No |
| 20 | No | No |
| 21 | No | No |
| 22 | No | No |
| 23 | No | Yes |
| 24 | Yes | — |
| 25 | Yes | — |
| 26 | No | — |
| 27 | No | — |
| 28 | No | — |
| 29 | No | No |
| 30 | Yes | — |
| 31 | No | No |
| 32 | No | No |
| 33 | No | Yes |
| 34 | No | No |
| 35 | No | Yes |
| 36 | Yes | — |
| 37 | No | No |
| 38 | No | No |
| 39 | Yes | — |
| 40 | No | No |
| 41 | Yes | — |
| 42 | Yes | — |
| 43 | No | No |
| 44 | Yes | — |
| 45 | Yes | — |
| 46 | No | No |
| 47 | Yes | No |
| 48 | Yes | — |
| 49 | No | No |
| 50 | Yes | — |
| 51 | Yes | — |
| 52 | Yes | — |
| 53 | No | No |
| 54 | No | Yes |
| 55 | No | No |
| 56 | No | No |
| 57 | No | No |
| 58 | No | No |
| 59 | No | No |
| 60 | No | No |
| 61 | No | No |
| 62 | No | No |
| 63 | No | No |
| 64 | No | No |
| 65 | Yes | — |
| 66 | No | No |
| 67 | Yes | — |
| 68 | Yes | — |
| number terminated | 24 | 6 |

[2]No = Failed to terminate
Yes = Terminated VT
35% 1st Bolus efficacy
15% 2nd Bolus efficacy
47% Overall Efficacy

EXAMPLE 5

A formulation of Example 1 (15mg/ml amiodarone in acetate buffer, pH 3.5–3.8) was evaluated in 23 patients (pts) (20 men, 3 women, ages 35–75, mean 60±14 yrs) following coronary angiography. Thirteen pts had coronary artery disease (CAD) or previous mycardial infarction (MI), 6 had hypertensive heart disease, 2 had dilated cardiomyopathy, 1 had valvular heart disease and 1 had undiagnosed chest pain. Mean left ventricular ejection fraction was 54±11% (range 30–70%). Measurements were obtained at baseline, immediately following each of two 150 mg IV doses of the formulation, i.e., about 10 ml, injected over 2–4 minutes (min), with a 5 min interdosing interval, and at 30 min following the second dose. The effects on heart rate (HR), mean arterial pressure (MAP), left ventricular end-diastolic pressure (EDP) and dP/dt were:

| | Baseline | Post 1st Dose | Post 2nd Dose | 30 Min |
|---|---|---|---|---|
| HR (bpm) | 72 ± 13 | 72 ± 12 | 72 ± 12 | 65 ± 12* |
| MAP (mmHg) | 91 ± 12 | 94 ± 16 | 96 ± 15 | 100 ± 17** |
| EDP (mmHg) | 18 ± 7 | 20 ± 9 | 22 ± 8 | 20 ± 8 |
| dP/dt (mmHg/s) | 1587 ± 603 | 1500 ± 531 | 1476 ± 686 | 1334 ± 568 |

*p = .0004 v. all others by ANOVA
**p = .008 vs baseline by ANOVA

There were no significant changes in QRS or $QT_c$ intervals. However, PR interval increased from baseline (177±32 to 187+35 ms; p=0.006). Five pts developed 1st degree AVB. No pts developed $2^{nd}$ or $3^{rd}$ degree AVB during the study. No proarrhythmic efects were noted.

Thus, 15 mg/ml amiodarone in 0.05 to 0.1 M acetate buffer, pH 3.5–3.8, given by rapid IV dosing, is not associated with hypotension, elevation of EDP, induction of heart failure, or proarrhythmia, and is better tolerated than currently available formulations of IV amiodarone.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for the treatment of a human patient suffering from arrhythmia comprising intravenously administering to the human patient an effective anti-arrhythmic quantity of a compound of the formula:

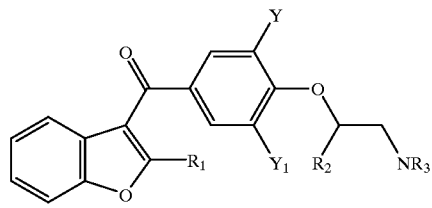

wherein $R_1$ is alkyl of 1–6 carbon atoms;
$R_2$ is hydrogen or methyl; and $NR_3$ is dimethylamino, diethylamino, dipropylamino, piperidino, pyrrolidino or morpholino; and
Y and $Y_1$ are hydrogen, iodo or bromo, the compound being dissolved in acetate buffer having a pH of from about 3.5 to 3.8 at a concentration of about 10 mg/ml to about 20 mg/ml.

2. A method for treating arrhythmia in a human patient in need of such treatment comprising intravenously administering to the patient, by rapid IV dosing, a composition comprising as an active ingredient about 10 mg/ml to about 20 mg/ml amiodarone in about 0.05 M to about 0.1 M acetate buffer having a pH of about 3.5 to about 3.8 wherein the treatment produces substantially no hypotension in the patient.

3. The method according to claim 2 wherein the composition comprises about 15 mg/ml amiodarone.

4. The method according to claim 2 wherein the composition comprises about 10 mg/ml amiodarone.

5. The method according to claim 2 wherein the treatment is associated with substantially no elevation of end-diastolic pressure or proarrhythmic effects in the patient.

6. A method for the treatment of a human patient suffering from arrhythmia comprising intravenously administering to the patient about 150 to about 300 mg of amiodarone as a composition comprising about 10 mg/ml to about 20 mg/ml of amiodarone in acetate buffer having a pH of about 3.5 to about 3.8.

7. The method according to claim 6, wherein the patient is intravenously administered about 150 mg amiodarone as a single bolus dosage.

8. The method according to claim 6, wherein the patient is intravenously administered about 300 mg amiodarone in two 150 mg bolus dosages.

\* \* \* \* \*

UNITED STATES PATENT AND TRADEMARK OFFICE
CERTIFICATE OF CORRECTION

PATENT NO. : 6,103,757
DATED : August 15, 2000
INVENTOR(S) : John C. Somberg

It is certified that error appears in the above-identified patent and that said Letters Patent are hereby corrected as shown below:

At column 1, line 17, delete "(P-N-diethylaminoethoxy)" and replace with --(Beta-N-diethylaminoethoxy)--.

Signed and Sealed this

Twenty-fourth Day of April, 2001

Attest:

NICHOLAS P. GODICI

Attesting Officer

Acting Director of the United States Patent and Trademark Office